(12) United States Patent
Salz et al.

(10) Patent No.: US 6,394,803 B1
(45) Date of Patent: May 28, 2002

(54) MIXING ARRANGEMENT

(75) Inventors: Ulrich Salz, Lindau (DE); Andre Rumphorst, Vaduz (LI); Alexandros Gianasmidis, Heerbrugg (CH); Frank Muller, Feldkirch (AT); Volker Rheinberger, Vaduz (LI)

(73) Assignee: Ivoclar AG, Schaan (LI)

( * ) Notice: Subject to any disclaimer, the term of this patent is extended or adjusted under 35 U.S.C. 154(b) by 0 days.

(21) Appl. No.: 09/695,000

(22) Filed: Oct. 24, 2000

Related U.S. Application Data

(60) Provisional application No. 60/183,577, filed on Feb. 18, 2000.

(30) Foreign Application Priority Data

Dec. 9, 1999 (DE) .......................................... 199 59 437

(51) Int. Cl.[7] .................................................. A61C 1/14
(52) U.S. Cl. ........................... 433/49; 433/77; 206/63.5
(58) Field of Search ............................... 433/49, 77, 80, 433/229; 206/524.3, 63.5

(56) References Cited

U.S. PATENT DOCUMENTS 5,106,297 A * 4/1992 Discko, Jr. .................. 433/77
5,749,730 A * 5/1998 Johnsen et al. ............. 433/163
5,947,278 A * 9/1999 Sawhney et al. ........... 206/216

FOREIGN PATENT DOCUMENTS

| DE | 37 33 799 A1 | | 4/1989 | |
|---|---|---|---|---|
| FR | 2595940 | * | 9/1987 | .................. 433/49 |
| GB | 380407 | * | 9/1932 | .................. 433/49 |

* cited by examiner

*Primary Examiner*—Cary E. O'Connor
(74) *Attorney, Agent, or Firm*—John C. Thompson; Alan S. Korman

(57) ABSTRACT

A mixing arrangement and method for mixing a substance for the field of dentistry are provided, with the production of the substance requiring at least one base material and one reactant. A catalyst is applied to a base surface as reactant in a solid or semi-solid layer. The unit comprising catalyst and base is prefabricated, and the base material, particularly in liquid form, can be applied or introduced to the base surface that is provided with the catalyst prior to using the substance. The substance can be applied ready for use by means of an application element after the catalyst and base material have been mixed.

16 Claims, 2 Drawing Sheets

MIXING ARRANGEMENT

This application claims priority from provisional application Ser. No. 60/183,577, filed Feb. 18, 2000.

BACKGROUND OF THE INVENTION

The present invention relates to a mixing arrangement for mixing a substance for the field of dentistry, the production of which substance requires at least one base material and one reactant. The present invention also relates to a method for mixing such a substance, particularly for mixing an adhesive, wherein the substance is produced from a base material and a reactant that are mixed together immediately prior to the substance being used.

Such a mixing arrangement is known from DE-OS 3 733 799. In this known solution a base is provided, the base comprising color basins in which coloring matter can be mixed. A plurality of color basins are provided next to each other in order to make it possible to compare the coloration achieved.

Numerous additional mixing arrangements comprising bases have become known in which either a component of a mixture is maintained and stored on the base in advance and an additional component is added at the time of application or in which both or, if applicable, all (i.e., more than one) components are mixed together on the base at the time of application.

Such bases can be flat or essentially basin-shaped in order to facilitate removal and the mixing process itself. The known mixing arrangements use bases in which the components to be mixed are applied in succession. The bases can be basin-shaped (see, e.g., DE-OS 3 733 799) or even flat, the mixing then being performed by means of a spatula or another suitable application element.

It has been suggested that the base be embodied as a disposable base, e.g., made of an economical plastic sheet, or made from a more substantial material, in which case the surface of the base can then as a rule be wiped off and cleaned well. Solid and re-usable bases are very economical in terms of material consumption in dental laboratories and dental practices. However, they require a certain amount of care during cleaning to prevent residual matter from the previous mixture from leaving contaminants. Apart from this, a re-usable base as a rule cannot be used for all substances mixed in the field of dentistry, particularly small amounts of substances whose proportions to each other are precisely regulated (e.g., adhesives).

Furthermore, it has already been suggested that a so-called single dose unit be prefabricated and that the dentist have available a prefabricated and packaged unit comprising the substances to be mixed, the application element, and the base, if any. The best solution in terms of packaging and manufacturing costs would be to produce a blister package that comprises the various openings for the substances and, e.g., even for the application element. However, if one of the substances to be mixed is a liquid, for instance, this solution is hardly practical because combining the individual substances that are each applied to the same base requires that the blister base be cut to permit additions to be made in the manner desired. This type of mixing however would necessarily be awkward and prone to contamination so that it has little market value, at least to this point in time.

Experienced dental technicians and dentists frequently favor containers that have been pre-filled with the substances to be mixed over single dose units. Although such solutions regularly require less complex packaging, the complexity of metering is greater, especially when it is important that mixing ratios be maintained. Pipettes and droppers that can handle small quantities have become known for liquids. Metering apparatus have also become known for powder substances, although these are frequently associated with high costs because a metering apparatus that is used for different substances must be cleaned after every process in which a substance is added in, and this would not be acceptable for a dental practice.

On the other hand, it is very important, particularly when using catalysts as reaction substances, that they be present in an active form (i.e., in a form in which a reaction cannot be triggered prematurely or when this is not desired—a reaction that substantially affects quality and safety when using an adhesive, for example), that the required reaction substances be combined in the defined ratio and in undiminished quality.

The object of the invention is therefore to create a mixing arrangement of the aforementioned general type and furthermore to create a method that combines the advantages of providing the substances to be mixed from containers and the advantages of a single-dose unit.

SUMMARY OF THE INVENTION

The mixing arrangement of the present invention is characterized primarily in that a catalyst is applied to a base surface as reactant in a solid or semi-solid layer and the unit comprising catalyst and base is prefabricated, and in that the base material, particularly in liquid form, can be applied or introduced to the base surface that is provided with the catalyst prior to using the substance, and in that the substance can be applied ready for use by means of an application element after the catalyst and the base material have been mixed.

In accordance with the invention, one of the substances required for the reaction, particularly a base material can be stored and maintained in a container, e.g., a bottle. Both the base and at least one other reaction substance, particularly a catalyst, can be provided in a type of single-dose unit, the special advantages in accordance with the invention resulting in that the reactant is already provided on the base so that there are no concerns about spillage when the reactant is applied to the base nor is awkward handling required for the single-dose unit. On the contrary, a basin in the blister base can be provided with the base material at once, e.g., in the form of a drop, and then the mixing required can be performed directly and on-site using the necessary application element.

This eliminates complex metering of the reactant, and, depending on the state of aggregation of the base substance in the particularly advantageous inventive embodiment, filling the basin can be used as an indicator for adding the base material. If, for instance, a solid or semi-solid catalyst is applied to the base and the base is basin-shaped, the metering can be coordinated such that to achieve the desired mixing ratio it is possible to fill the basin up to the border line of the reactant layer drawn up the side face. If, on the other hand, the reactant applied to the base is semi-solid and a liquid substance is to be introduced as the base substance, it is also possible to provide the application element with a metering basin like a type of spoon that permits measuring without the use of any specially embodied metering apparatus.

In accordance with a particularly advantageous embodiment of the inventive mixing arrangement, it is provided that the catalyst or the other reactant is prefabricated in a closed container as a single-dose unit. This solution ensures that the more sensitive of the substances is maintained until it is used, particularly under an air seal, so that even for extended periods of storage there is no reason to be concerned about a diminution in the quality of the substances required for the reaction.

Nevertheless, the base substance can be added from a container, e.g., a bottle. For instance, one or more drops can be added from a bottle with adhesive to the basin in which the catalyst film is located and the catalyst is dissolved and incorporated.

In this context it is particularly advantageous that in accordance with the invention even the form of the solid reactant can be adapted to the mixing ratio and the base substances available. An appropriate predetermined volume is established for the basin and used as the base for the inventive mixing arrangement.

In this context it is particularly advantageous when the targeted degree of filling relative to the entire system is at least 20%, comprising reactant or reactants and base material. A degree of filling that approaches approximately 50% contributes to improving the thoroughness of mixing (given an equal number and intensity of the stirring strokes), it being understood that in accordance with the invention it is preferred that a solid or semi-solid substance is mixed with at least a semi-liquid substance, preferably a liquid substance.

As a rule, it is advantageous when the basin comprises radii at the transition between the side faces and bottom surface in order to improve the thoroughness of mixing. The radii are preferably dimensioned such that they fit the nose radius of the enclosed application element in order to simplify handling.

This solution is particularly useful in the advantageous embodiment of the mixing arrangement that provides in the basin in one packaging unit both the accessory application element in a compartment and the base that is already provided with the reactant.

It is to be understood that the shape of the basin, particularly the height/width ratio, can be adapted to requirements in many fields. Thus the basin can be embodied as a base surface that is flat, slightly concave, or highly concave. The basin can be covered with a sealing foil or a plurality of basins can be covered with one foil that can be pulled off by individual basin, if necessary.

In a particularly advantageous embodiment of the inventive mixing arrangement it is provided that the basin and the compartment are covered and sealed by a common sealing foil that can then be removed in one pull. This embodiment is particularly suitable for employment in a safe and simple manner. The user pulls the sealing foil off and removes the application element from the compartment. The base material is added to the reactant up to the specified marking and stirred briefly with the application element. Then the finished substance is applied to a surface by means of the application element. Such surfaces are, e.g., dental cavities, the surfaces of teeth, root canals, but such surfaces can also be technical dental restorations like crowns. Once the treatment has concluded, the application element can be replaced in the compartment and the basin can be resealed by pressing the sealing back onto it. In this manner the mixing arrangement can be disposed of with no contamination, even if there is still residual mixed, finished substance remaining in the basin. Required for this solution is the realization of re-closable packaging, e.g., blister packages. Appropriate heat-sealable media are known in and of themselves.

The invention is particularly important for light-curing and dual-curing (light- and self-curing) dentin protectors, cements, or adhesives such as are employed, e.g., in filling technology for composites or for cementing crowns. When using these materials, three catalysts are necessary (e-g., camphorquinone for light-curing, peroxide and amine for self-curing). Since these three catalysts cannot be stored in one material, the only option is to mix together two (if not three) liquids or pastes before the material is employed for its purpose. Using the present invention it is possible to store in one basin one or two catalysts as solid or semisolid substances in a surface coating and to produce, e.g., a dual-hardening adhesive by adding a liquid that contains an additional catalyst.

BRIEF DESCRIPTION OF THE DRAWING

Additional advantages, details, and features can be found in the following description of two embodiments, with reference to the accompanying drawings, in which.

DESCRIPTION OF PREFERRED EMBODIMENTS

Figure 1:
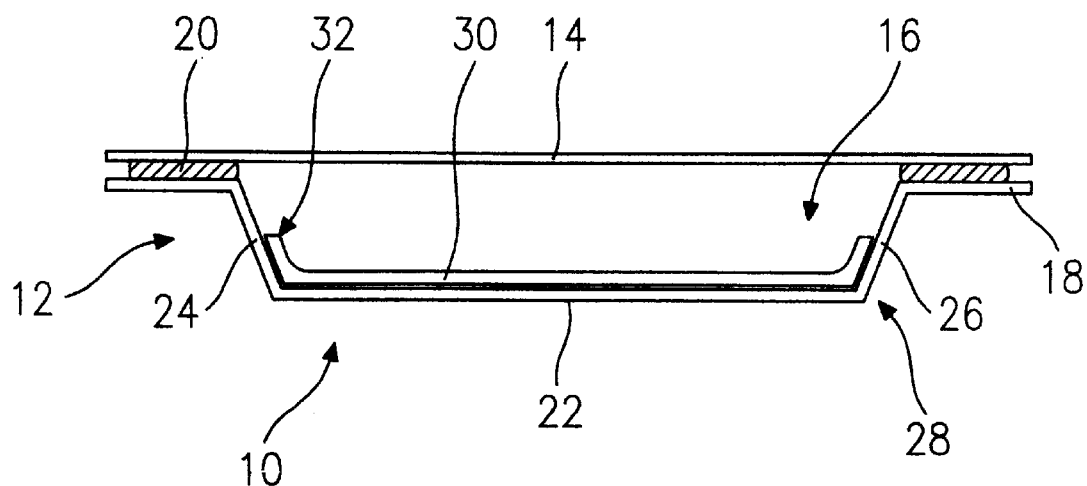
FIG. 1 illustrates a section through a first embodiment of a mixing arrangement in accordance with the invention wherein a solid reactant is shown.

The mixing arrangement 10 illustrated in FIG. 1 is embodied as a blister package. It comprises a blister base 12 and a sealing foil 14. The blister base 12 is deep-drawn in a manner known in and of itself and consequently comprises a basin 16. Flanged rims 18 of the blister base 12 encircle the basin 16. The flanged rims 18 are provided with adhesive 20 on their upper side, the adhesive application 20 extending entirely around the basin 16 and providing a zeal against the outside. The adhesive 20 thus bonds the flanged rim 18 to the sealing foil 14.

Figure 2:
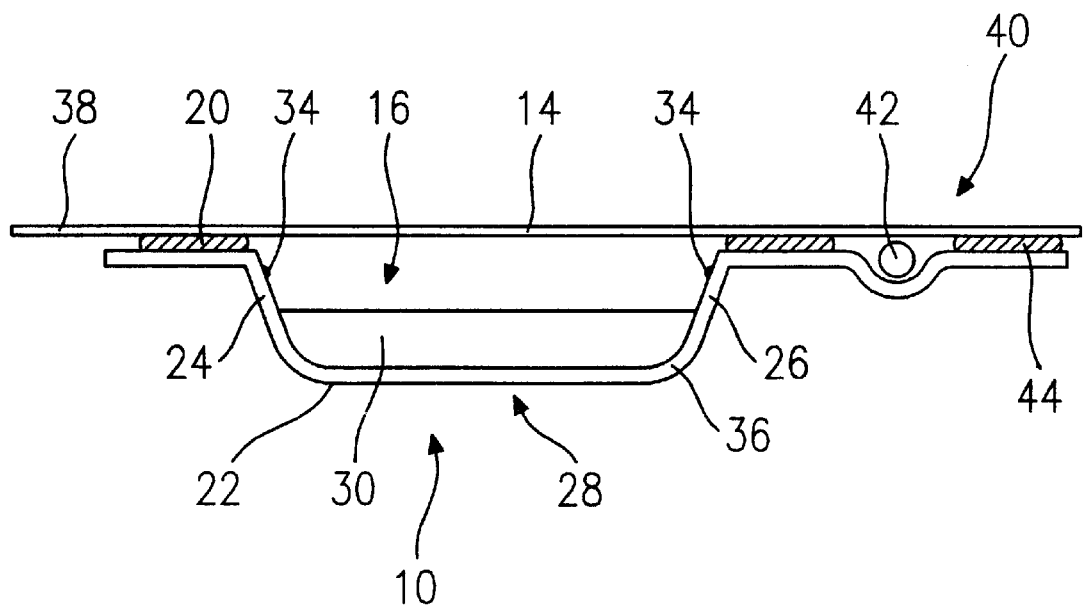
FIG. 2 illustrates a section through a second embodiment of a mixing arrangement in accordance with the invention wherein a semisolid reactant is shown.

In an embodiment modified from the illustration in FIG. 1, the sealing foil 14 is heat-sealable and is bonded to the flanged rim 18 by means of heat. In both cases it is advantageous for the sealing foil 14 to extend at one position in a manner known in and of itself to create a tear tab, as can be seen in FIG. 2.

The inventive basin 16 comprises a bottom surface 22 and two side faces 24 and 26. The side faces 24 and 26 diverge slightly in an outward direction, at an angle that is approximately 20° from the vertical. The bottom surface 22 and parts of the side faces 24 and 26 together constitute a base surface 28. In accordance with the invention, the bottom surface 22 and also the lower part of the side faces 24 and 26 are coated with a reactant 30, e.g., a catalyst. In the exemplary embodiment illustrated in FIG. 1, the catalyst is solid and is applied at once during manufacture in that it is provided with a solvent and introduced into the basin 16 and in that the solvent is evaporated. This is how the coating in FIG. 1 is formed; it exhibits slight rounding in the corners between side faces 24, 26 and bottom surface 22. If necessary, a plurality of layers with a plurality of catalysts can also be applied successively. It is also possible to realize one layer with two catalysts in a mixture so that both catalysts are applied simultaneously and are available for the reaction simultaneously.

When the solvent is evaporated, care is taken that the inventive mixing arrangement is standing on a horizontal surface. This results in a symmetrical and sharply delineated limit 32 up to which the catalyst 30 reaches on the side face 24, 26. This limit 32 can also serve as the fill line for the substance to be added during application. The catalyst or catalysts can also be applied to the surface by means of a freeze-drying process.

Consequently when this component (which preferably comprises base material) is added, the only consideration that must be taken into account is that the limit 32 is the fill line. This solution is consequently particularly suitable when the base material is liquid.

An embodiment that has been modified relative thereto is illustrated in FIG. 2. In this solution, a semi-solid reactant 30 is employed and the base material can be either viscous or liquid. Markings 34 are provided that indicate the height to which the base material should be added in order to ensure the correct mixing ratio.

The exemplary embodiment illustrated in FIG. 2 comprises substantially the same parts that were explained using FIG. 1, so that equivalent or corresponding reference numbers were used and no explanation is required.

Going beyond FIG. 1, the transition of the base 28 between the bottom surface 22 and the side faces 24, 26 comprises curves 36 that facilitate thorough blending during stirring. In addition, the sealing foil 14 is extended to form a tab 38. The basis of the particularity of the embodiment in accordance with FIG. 2 is that, in addition to the basin 16, a compartment 40 is provided that can accommodate an application element 42. The compartment 40 is also sealed by means of additional application of adhesive 44 or by means of another sealing agent so that the application element 42 is also protected against contamination during storage.

In this embodiment the sealing foil 14 can be opened by pulling the tab 38 in a single motion, this also uncovering the application element 42. The base material is added in liquid or, if necessary, in solid form, possible liquid forms ranging from very thin liquid to thick/very viscous liquid, and the application element 42 simultaneously serving as a stirrer for mixing.

Furthermore, with this embodiment selecting a suitable adhesive to ensures that the sealing foil 14 can be re-sealed so that it is possible to dispose of the mixing arrangement 10 with no contamination.

Figure 3:
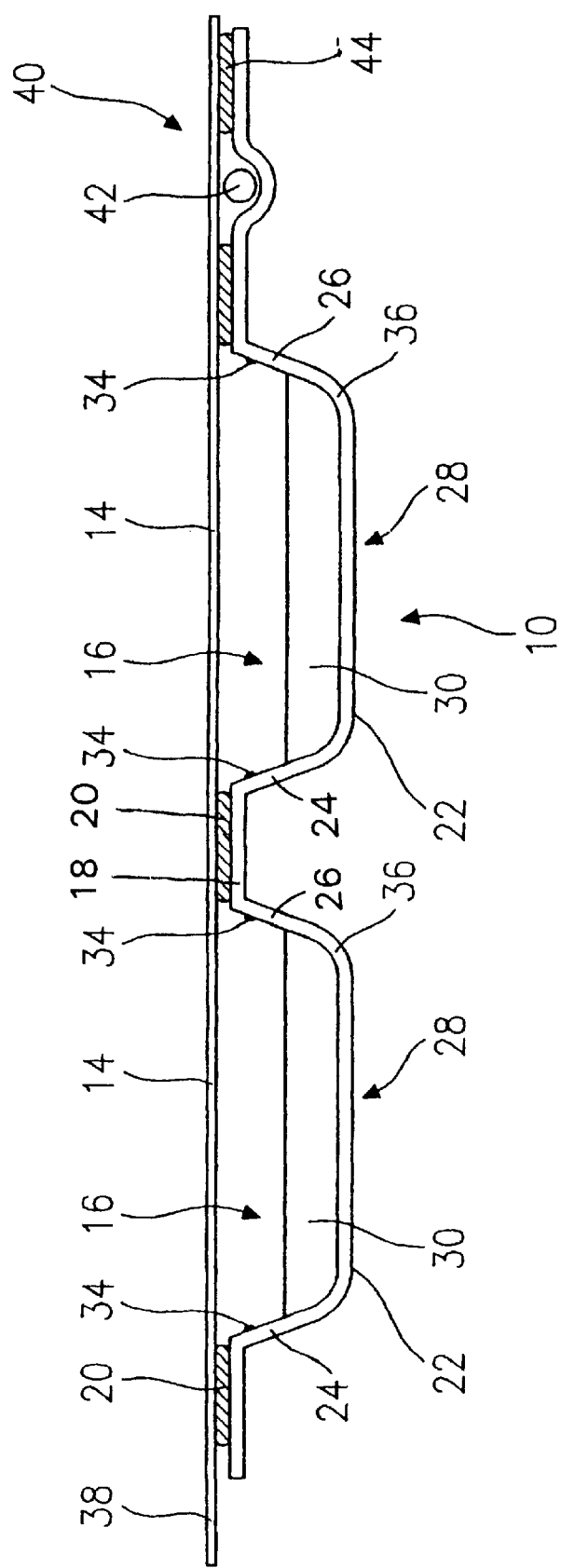
FIG. 3 illustrates a section through a third embodiment of a mixing arrangement in accordance with this invention wherein multiple basins are produced together and are interconnected by means of separators, semisolid reactants being shown.

FIG. 3 illustrates a section through a third embodiment of a mixing arrangement in accordance with this invention wherein multiple basins 16 are produced together and are interconnected by means of separators in the form of a centrally located flanged rim 18 and adhesive 20. In this design, semisolid reactants 30 are shown.

The present invention is, of course, in no way restricted to the specific disclosure of the specification and drawings, but also encompasses any modifications within the scope of the appended claims.

What we claim is:

1. A mixing arrangement for mixing a substance for the field of dentistry, the production of which substance requires at least one base material and one reactant, comprising:
   a catalyst applied to a base surface as reactant in a solid or semi-solid layer;
   a unit comprising catalyst and base and being prefabricated, wherein said base material, can be applied or introduced to said base surface that is provided with said catalyst prior to using said substance; and
   an application element for applying said substance ready for use after said catalyst and base material have been mixed.

2. A mixing arrangement according to claim 1, wherein said based surfaces are shaped like a basin or bowl and comprises a bottom surface that is essentially flat or concave.

3. A mixing arrangement according to claim 1, wherein at least one catalyst is applied to said base surface, where it forms a semi-solid or solid layer.

4. A mixing arrangement according to claim 1, wherein said base surface is produced from a thin sheet in a deep-draw or injection molding process, and wherein said catalyst is applied by means of coating in a deep-drawn region.

5. A mixing arrangement according to claim 4, wherein said catalyst extends over a bottom surface and at least partially over side faces of a basin.

6. A mixing arrangement according to claim 5, wherein said catalyst comprises a solid or semi-solid layer that fills said basin to less than 20%, and wherein said coating of said basin is drawn up said side faces until an end of said coating simultaneously forms a fill line for a correct mixing ratio for the mixing in of said base material.

7. A mixing arrangement according to claim 5, wherein said catalyst comprises a solid or semi-solid layer that fills said basin to a slight extent, and wherein said coating of said basin is drawn up said side faces until an end of said coating simultaneously forms a fill line for a correct mixing ratio for the mixing in of said base material.

8. A mixing arrangement according to claim 1, wherein said catalyst is accommodated in a deep-drawn thin sheet in the manner of a blister package.

9. A mixing arrangement according to claim 8 wherein the blister package is sealed by means of a separable sealing film.

10. A mixing arrangement according to claim 1, wherein said base material is an adhesive and is self-curing with the addition of at least one catalyst.

11. A mixing arrangement according to claim 1, which comprises multiple basins that are produced together and are interconnected by means of separators.

12. A mixing arrangement according to claim 1, wherein said base surface is provided with a compartment for said application element, and wherein a basin and said compartment are mutually closed off by a removable covering film.

13. A mixing arrangement according to claim 1, wherein said catalyst is provided with a color indicator that changes color when said base material is added in the correct mixing ratio.

14. A mixing arrangement according to claim 1, wherein two or more catalysts are applied to said base surface, where they form a semi-solid or solid layer.

15. A method for mixing a substance for the field of dentistry, particularly for mixing an adhesive, wherein the substance is produced from a base material and a reactant that are mixed together immediately prior to the substance being used, said method including the steps of:
   providing said reactant as at least one catalyst;
   initially applying said at least one catalyst to a base surface in a solid or semi-solid layer;
   thereupon closing and sealing said base surface;
   for applying said substance, exposing said base surface;
   adding said base material to said at least one catalyst; and
   after a brief reaction period, and if necessary after stirring, applying the substance that is produced to a tooth or a dental prosthesis by means of an application element.

16. A method according to claim 15, which includes a step of allowing said substance to harden on said tooth or dental prosthesis.

* * * * *